United States Patent [19]

Amiral

[11] Patent Number: 5,466,582
[45] Date of Patent: Nov. 14, 1995

[54] THROMBOCYTOPENIA DETERMINATION

[75] Inventor: Jean Amiral, Franconville, France

[73] Assignee: Serbio, Gennevilliers, France

[21] Appl. No.: 313,391

[22] Filed: Sep. 27, 1994

Related U.S. Application Data

[63] Continuation of Ser. No. 844,607, Apr. 8, 1992, abandoned.

[30] Foreign Application Priority Data

Aug. 9, 1990 [FR] France ................................ 90 10190

[51] Int. Cl.$^6$ ...................... G01N 33/535; G01N 33/536; G01N 33/541
[52] U.S. Cl. .................. 435/7.9; 435/28; 435/13; 435/961; 435/188; 436/536; 436/540; 436/164; 436/811
[58] Field of Search ..................... 435/7.9, 7.92, 435/28, 13, 188, 810, 961; 436/518, 540, 541, 178, 811, 536

[56] References Cited

U.S. PATENT DOCUMENTS

| 4,543,339 | 9/1985 | O'Neill | 436/510 |
| 4,844,895 | 7/1989 | Thorbecke et al. | 424/88 |

FOREIGN PATENT DOCUMENTS 0165681  12/1985  European Pat. Off. .

OTHER PUBLICATIONS

Sigma catalog 1989 p. 1212.
Huang et al, J. Biol Chem 257(19):11546–11550 Oct. 10, 1982.
Moore et al, Biochim Biophys Acta 379:370–384 1975.
McVey, D. S. et al "Detection of Antiplatelet Immunoglobulin in Thrombocytopenic Dogs" Veterinary Immunology and Immunopathology 22:101–111 1989.

*Primary Examiner*—Toni R. Scheiner
*Assistant Examiner*—Nancy J. Parsons
*Attorney, Agent, or Firm*—Evenson, McKeown, Edwards & Lenahan

[57] ABSTRACT

The present invention relates to the determination of thrombocytopenia induced by an inductor drug such as heparin. According to the invention, a sample is mixed with a complex of an antigenic substance such as platelet factor 4 (pF4) and heparin to determine if the sample contains antibodies which react with the complex. The presence of these antibodies is indicative of heparin-induced thrombocytopenia.

11 Claims, No Drawings

THROMBOCYTOPENIA DETERMINATION

This application is a continuation of U.S. application Ser. No. 07/844,607 filed Apr. 8, 1992, now abandoned.

FIELD OF THE INVENTION

The present invention relates to the use of a particular antigenic substance in the determination of thrombopenia (also called thrombocytopenia). It further relates to an improved method of determining this disease, notably the forms induced by various inductor drugs, in particular by quinine/quinidine (i.e. induced by quinine, its diastereoisomer quinidine and mixtures thereof) and especially by heparin.

PRIOR ART

It is known, especially from the article by M. C. BERNDT et al., Blood Reviews, 1, pages 111–118 (1987), that thrombopenia can be induced by numerous drugs and that the most frequent forms are caused by quinine/quinidine and especially heparin.

It is known that heparin is administered to hospitalized patients as an anticoagulant to prevent any risk of venous or arterial thrombus. Statistically it is known that (i) at least 50% of hospitalized patients are given heparin by injection, and that (ii) 1 to 5% of patients undergoing heparin therapy suffer from thrombopenia capable of developing particularly severely between the 5th and 15th days of the heparin therapy. Reference may be made in this connection to the articles by J. G. KELTON et al., Blood, 72 (n° 2), pages 925–930 (1988);
B. H. CHONG et al., British Journal of Haematology, 49, pages 531–540 (1981);
B. H. CHONG, Blood Reviews, 2, pages 108–114 (1986);
D. SHERIDAN et al., Blood, 67, (n° 1), pages 27–30 (1986);
Y. GRUEL, Sang Thrombose Vaisseaux, 1 (n° 4), pages 233–236 (1989);
M. SAMAMA et al., Journal des Maladies Vasculaires, 7, pages 237–242 (1982); and
J. CONARD et al., entitled: "Les thrombopénies á l'héparine" ("Heparin-induced thrombopenia") and published in the work "Progrés en Hématologie 4, Les Plaquettes Sanguines" ("Progress in Hematology 4, Blood Platelets"), pages 107–118, published by Doin, Paris (1983).

In patients benefitting from heparin therapy and developing thrombopenia, two forms are known:

so-called slight or moderate forms of thrombopenia which are asymptomatic, and so-called severe forms of thrombopenia which are frequently accompanied by arterial or venous thromboembolic complications resulting from the appearance of antibodies directed against platelets in the presence of heparin.

This appearance of antibodies is illustrated especially in the article by D. M. LYNCH et al., Blood, 66 (n° 5), pages 1176–1181 (1985), and in the aforementioned articles by M. C. BERNDT et al., J. G. KELTON et al., B. H. CHONG et al., B. H. CHONG, D. SHERIDAN et al. and J. CONARD et al. (see, in particular, the mechanism of heparin-induced thrombopenia presented in Table III on page 115 of said article by J. CONARD et al.).

The problem of the prophylaxis of the disease thrombopenia has not yet been solved. There is nevertheless a need for a rapid and reliable assay method which makes it possible to assess the risk of the development of thrombopenia so that the administration of the inductor drug can be stopped sufficiently early.

At the present time, the methods used for the diagnosis of thrombopenia comprise (1) searching for the absence of an etiology other than thrombopenia (infections, other therapies, etc.), which is long and tedious, (2) counting the blood platelets before, during and after treatment, which is long and rather unspecific, or (3) the biological tests (referred to below) which test for the appearance of antibodies directed against platelets in the presence of the inductor drug.

It is found that the biological examinations in most frequent use are the platelet aggregation tests, which require adapted equipment and involve procedures which are long and in certain cases lacking in sensitivity.

The other methods referred to in section (3) above, which have been described (see, in particular, the afore-mentioned articles by J. G. KELTON et al., B. H. CHONG et al., B. H. CHONG, D. SHERIDAN et al., D. M. LYNCH et al. and Y. GRUEL), involve the study of the platelet binding of serum IgGs, the release of $^{14}C$-radiolabeled serotonin at two different heparin concentrations, the availability of platelet factor 3, the binding of complement, the inhibition of the lysis of complement and the agglutination of sensitized erythrocytes (especially sheep erythrocytes). It is found that these biological assay methods are either a) rather insensitive or rather unreliable, or b) if they are sensitive, lengthy to carry out.

AIM OF THE INVENTION

According to a first feature of the invention, a novel technical solution is proposed for the determination of thrombopenia induced by an inductor drug (Z). This novel technical solution is based on the detection, (i) by means of a specific antigenic substance (Ag), (ii) of an antibody-type immunological material contained in the plasma of the subject to be tested and selected from the group consisting of anti(Y) antibodies (where Y is especially Z or Z-Ag complexes) directed especially against the inductor drug Z and its complexes with Ag.

In the light of the results of the work undertaken by the Applicant, it has been found that in warm-blooded animals, especially man and other mammals, the administration of a thrombopenia-inducing drug produces anti(Z), anti(Z-platelet), anti(Z-Ag) and anti(Z-Ag-platelet) antibodies leading to blood platelet aggregation or activation and causing thrombopenia.

The novel technical solution according to the invention for the determination of thrombopenia uses an antigenic substance (Ag) obtained especially by cleavage or lysis of blood platelets and having a strong affinity for the inductor drug, said antigenic substance being intended to react with an anti(inductor drug) antibody by the following mechanism:

$$Ag_1 + anti(Y) \rightarrow Ag_1\text{-}anti(Y) \qquad (1)$$

where $Ag_1$ denotes said antigenic substance Ag or complexes containing said antigenic substance, and anti(Y) denotes an antibody material contained in the plasma to be tested and directed against the inductor drug Z and complexes in which it is present (especially $Z\text{-}Ag_1$, Z-platelet and $Z\text{-}Ag_1$-platelet complexes), which produce blood platelet aggregation or activation and cause thrombopenia.

In contrast to the solutions known in the prior art, this novel technical solution offers the advantage of being reliable, very sensitive and rapid to carry out.

The result of reaction (1) above can be detected, indicated or amplified by a method known per se (especially by agglutination, EIA, RIA or FIA).

According to a second feature of the invention, a method is recommended for the reliable and rapid determination of thrombopenia induced by any inductor drug, in particular quinine/quinidine and especially heparin.

SUBJECT OF THE INVENTION

It is therefore proposed, according to the invention, to use an antigenic substance in the determination of thrombopenia induced by an inductor drug (Z), in which use said antigenic substance is selected from the group consisting of fractions which (i) are present in blood platelets and released from said blood platelets by cleavage or lysis, and (ii) have a strong affinity for the inductor drug (Z) and/or complexes of said inductor drug with platelets, and said antigenic substance is intended to react with an anti(Y) antibody material contained in the plasma to be tested and directed against the inductor drug, its fragments or products containing said inductor drug or one of its fragments.

Such a use is suitable for any drug (Z) inducing thrombopenia of immune origin, especially paracetamol, acetazolamide, aspirin, allylisopropylcarbamide, alprenolol, amrinone, antazoline, bleomycins, carbamazepine, cephalothine, chlorothiazide, chlorpropamide, cimetidine, clonazepam, sulfonamides (especially sulfamethoxazole, sulfamethazine, sulfamethoxypyridazine, etc.), sulfonamide-trimethoprim combinations (especially the sulfamethoxazole-trimethoprim combination in a weight ratio of 5/1), DDT, desipramine, diazepam, digitoxin, diphenylhydantoin, fenoprofen, heroin, hydrochlorothiazide, isoniazide, L-(–)-tetramisole, levodopa, lignocaine, meprobamate, methicillin sodium, minoxidil, morphine, novobiocin, organic arsenic derivatives, oxyphenbutazone, oxprenolol, p-aminosalicylic acid, penicillins, procainamide, prochlorperazine, propylthiouracil, rifampicin, spironolactone, stibophen, sulindac and tolbutamide.

This use is particularly advantageous in the determination of the most frequent forms of thrombopenia, which are induced by quinine/quinidine and especially heparin.

A method is recommended for the determination of thrombopenia induced by any inductor drug (Z), said method comprising reaction (1) given above, in which the anti(Y) antibody material is directed against the inductor drug Z, substances containing said inductor drug (especially Z-$Ag_1$, Z-platelet or Z-$Ag_1$-platelet complexes and polymers of Z), substances derived from or analogous to Z (especially fragments of Z and metabolites of Z), products containing said substances derived from or analogous to Z (especially their complexes), or mixtures thereof.

Finally, according to the invention, assay kits are proposed for the determination of thrombopenia, said kits comprising at least one sample of said aforementioned antigenic substance or one of its complexes and, if appropriate, appropriate dilution media and/or other reagents.

ABBREVIATIONS

The following abbreviations have been used hereafter for convenience:

| | |
|---|---|
| Ag | denotes the antigenic substance according to the invention, which has a strong affinity for the inductor drug Z; |
| $Ag_1$ | denotes said antigenic substance Ag and complexes in which it is present; |
| anti(Z) | denotes an antibody generated against the inductor drug (Z); |
| anti(X) | denotes any antibody generated against the substance X; thus anti(Z), anti(Ig), anti(IgA), anti(IgG) and anti(IgM) respectively denote any antibody generated against the inductor drug Z; immunoglobulins Ig, IgAs, IgGs and IgMs; |
| EIA | denotes an enzyme immunoassay; |
| ELISA | denotes an enzyme-linked immunosorbent assay, which is a particular EIA technique; |
| F(ab) | denotes a first antibody fragment obtained by cleavage of said antibody with papain; |
| $F(ab')_2$ | denotes a second antibody fragment obtained by cleavage of said antibody with pepsin; |
| Fc | denotes any antibody fragment separated from the fragment F(ab) by cleavage with papain or separated from the fragment $F(ab')_2$ by cleavage with pepsin; said fragments Fc are homologous but structurally slightly different according to whether they have been cleaved with papain or pepsin (the structure and the method of obtaining F(ab), $F(ab')_2$ and Fc are illustrated in French patent application n° 89 04 589 filed on April 7, 1989); |
| FIA | denotes a fluorescent immunoassay; |
| Hep | denotes heparin, its derivatives or its analogs (including their complexes with platelets); |
| HRGP | denotes a histidine-rich glycoprotein; |
| Ig | denotes any immunoglobulin; |
| IgA | denotes any immunoglobulin A; |
| IgG | denotes any immunoglobulin G; |
| IgM | denotes any immunoglobulin M; |
| LA-pF4 | denotes a precursor of βTG (low-affinity pF4); |
| MW | denotes the molecular weight; |
| OD | denotes the optical density (measured especially at a wavelength of 492 nm); |
| OPD | denotes orthophenylenediamine; |
| PBP | denotes the precursor of LA-pF4, namely platelet basic protein; |
| pF3 | denotes platelet factor 3; |
| pF4 | denotes platelet factor 4; |
| POD | denotes peroxidase; |
| Qn/Qnd | denotes quinine, quinidine, mixtures thereof and corresponding derivatives or analogs; |
| R* | denotes a labeling means; |
| RF | denotes the rheumatoid factor; |
| RIA | denotes a radioimmunoassay; |
| RT | denotes room temperature (15–25° C.); |
| βTG | denotes beta-thromboglobulin resulting from the degradation or partial cleavage of LA-pF4; |
| Y | denotes the inductor drug Z, products in which it is present and its derivatives and/or analogs; |
| Z | denotes the thrombopenia-inducing drug. |

DETAILED DESCRIPTION OF THE INVENTION

The present invention relates to the determination of thrombopenia of immune origin.

The antigenic substance $Ag_1$ according to the invention encompasses on the one hand the antigenic material Ag consisting of platelet fragments (including the walls), intraplatelet fractions which can be released from blood platelets by cleavage or lysis, and, if appropriate, plasma or blood substances, and on the other hand complexes of said platelet fragments, said intraplatelet fractions and said plasma or blood substances.

The expression "having a strong affinity for the inductor drug Z", applied to the antigenic substance, is understood as meaning that the antigenic substance Ag easily reacts with the inductor drug Z, derivatives of Z, analogs of Z and products containing Z.

In view of the affinity of Ag for the inductor drug Z, derivatives of Z (especially metabolites), analogs of Z (especially heparinoids when Z is Hep) and products containing Z, all the products and complexes included in the definition of $Ag_1$ are obtained.

A novel use of an antigenic substance is recommended for the determination of thrombopenia induced by an inductor drug such as (a) heparin or (b) quinine/quinidine, in particular for the determination of the most frequent forms of thrombopenia, in which use said antigenic substance is selected from the group consisting of fractions which (i) are platelet fractions obtained especially by cleavage or lysis of blood platelets, and (ii) have a strong affinity for (a) Hep or (b) Qn/Qnd, and said antigenic substance is intended to react with an (a) anti-heparin or, respectively, (b) anti-quinine/quinidine antibody material contained in the plasma to be tested and directed against (a) Hep or Hep-platelet, Hep-antigenic substance and/or Hep-antigenic substance-platelet complexes, or, respectively, (b) Qn/Qnd or Qn/Qnd-platelet, Qn/Qnd-antigenic substance and/or Qn/Qnd-antigenic substance-platelet complexes, where Hep is heparin, compounds derived from heparin, compounds analogous to heparin or mixtures thereof, and Qn/Qnd is quinine/quinidine, compounds derived from quinine/quinidine, compounds analogous to quinine/quinidine or mixtures thereof, said antibody material producing blood platelet aggregation or activation and causing thrombopenia.

Bearing in mind the definitions given above, when the inductor drug Z is heparin, the term Hep encompasses any product selected from the group consisting of heparin itself, having an average MW of 6000–30,000 daltons and an optical rotation $[\alpha]_D^\circ$ of about +55°;

heparin derivatives, especially metal heparinates ($Ca^{2+}$, $Li^+$, $Na^+$, $Mg^{2+}$, etc.) and heparin fragments;

heparin analogs, especially heparinoids (heparamine and its salts, chondroitins and their salts, etc.) and heparins having an average molecular weight of less than 6000 daltons;

substances containing heparin and its derivatives and analogs, especially complexes of heparin and of its derivatives and analogs; and mixtures thereof.

As indicated above, the method according to the invention for the determination of thrombopenia induced by an inductor drug (Z) comprises reacting (A) an antigenic substance ($Ag_1$) selected from the group consisting of (i) fractions (Ag) which have a strong affinity for the group consisting of (a) the inductor drug, (b) its derivatives, (c) its analogs, (d) products containing Z, its derivatives or its analogs, or (e) mixtures thereof, and which are obtained especially by cleavage or lysis of blood platelets; and (ii) substances containing at least one Ag-Z complex, with (B) an anti(Y) antibody material, where anti(Y) is an antibody material directed against (a) Z, (b) derivatives of Z, (c) analogs of Z, (d) products containing Z, its derivatives or its analogs, or (e) mixtures thereof.

The anti(Y) antibody material will preferably be selected from the group consisting of anti(Z), anti(Z-platelet), anti(Z-Ag) and anti(Z-Ag-platelet) antibodies; in practice the plasma of the patient to be tested will be used as the source of the anti(Y) material, which generally contains anti(Z) and especially anti(Z-Ag) antibodies.

To carry out reaction (1) given above, the Ag-Z complex will first be prepared by reacting Ag with Z, and then the following reaction will be carried out:

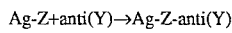

It has furthermore been found that when starting from an antigenic substance $Ag_1$ comprising the Ag-Z complex, the sensitivity of the assay is improved by adding an appropriate amount of the inductor drug Z to said complex.

According to the invention, for the determination of thrombopenia induced by (a) heparin or (b) quinine/quinidine, a method is recommended which involves reacting an antigen (1), which is specific for the autoantibody (2) generated by the inductor drug after administration of the latter, with said autoantibody (2), in which method said antigen (1) is an antigenic substance ($Ag_1$) selected from the group consisting of (i) fractions (Ag) which have a strong activity towards the group consisting of (a) heparin, (b) its derivatives, (c) its analogs, (d) products containing heparin, its derivatives or its analogs, or (e) mixtures thereof, or, respectively, towards the group consisting of (a) quinine/quinidine, (b) its derivatives, (c) its analogs, (d) products containing quinine/quinidine, its derivatives or its analogs, or (e) mixtures thereof, which are obtained especially by cleavage or lysis of blood platelets; and (ii) substances containing at least one complex of said fraction (Ag) with Hep or, respectively, Qn/Qnd, where Hep and Qn/Qnd are defined as indicated above.

In this particular method relating to the determination of thrombopenia induced by heparin or quinine/quinidine, the autoantibody (2) is selected, as indicated above, from anti-(Hep), anti(Hep-platelet), anti(Hep-$Ag_1$) and anti(Hep-$Ag_1$-platelet) antibodies or, respectively, from anti(Qn/Qnd), anti(Qn/Qnd-platelet), anti(Qn/Qnd-$Ag_1$) and anti(Qn/Qnd-$Ag_1$-platelet) antibodies, the preferred autoantibodies being those directed against at least one complex of the inductor drug with the means Ag.

For the determination of heparin-induced thrombopenia, said antigenic substance Ag will be selected from the group consisting of (A) platelet factor 4 (pF4), (B) fractions containing pF4, (C) fractions containing at least one substance eluted at the same time as pF4, (D) recombinant pF4 and its variants, (E) synthetic peptides reproducing all or part of the amino acid sequence of pF4 (in particular the carboxy-terminal peptides 1–13 or 13–24), (F) proteoglycan, (G) proteoglycan-pF4 complexes, and (H) mixtures thereof.

Among the fractions containing pF4, referred to as the means (B) above, there may be mentioned especially pF4 polymers comprising several parallel chains of monomeric pF4.

Among the fractions containing at least one substance eluted at the same time as pF4, referred to as the means (C) above, there may be mentioned especially the substances PBP, LA-pF4, βTG and mixtures thereof.

Among the proteoglycan-pF4 complexes, referred to as the means (G) above, there may be mentioned especially the complex consisting of dimeric proteoglycan in which each proteoglycan group is bonded to four tetrameric pF4 groups, and having an average molecular weight of 368,000 daltons, said complex also being called the "native form of pF4" and having a strong affinity for heparin. Said complex can be represented by the following formula:

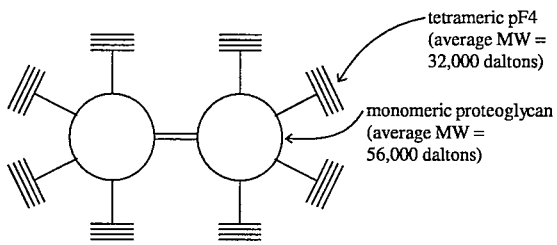

The antigenic substances Ag which are particularly preferred for the determination of heparin-induced thrombopenia are selected from the group consisting of monomeric pF4 having an average molecular weight of 8000 daltons, polymeric pF4, especially tetrameric pF4 having an average molecular weight of 32,000 daltons, proteoglycan having an average molecular weight of 56,000 daltons, proteoglycan-pF4 complexes, especially the complex consisting of dimeric proteoglycan in which each proteoglycan group is bonded to 4 tetrameric pF4 groups, and having an average molecular weight of 368,000 daltons, and mixtures thereof.

According to the best mode of carrying out the invention, it is advantageously preferable to use antigenic substances $Ag_1$ which are complexes of said aforementioned substances Ag with Hep.

Within the framework of the determination of heparin-induced thrombopenia, the carrying-out of reaction (1) given above comprises 1°) the formation and/or activation of the antigenic substance according to the mechanism $$Ag+Hep \rightarrow Ag\text{-}Hep \qquad (2)$$

2°) one of the corresponding reactions $$Ag\text{-}Hep+anti(Hep) \rightarrow Ag\text{-}Hep\text{-}anti(Hep) \qquad (3)$$

$$Ag\text{-}Hep+anti(Hep\text{-}Ag) \rightarrow Ag\text{-}Hep\text{-}anti(Hep\text{-}Ag) \qquad (4)$$

$$Ag\text{-}Hep+anti(Hep\text{-}Ag\text{-}platelet) \rightarrow Ag\text{-}Hep\text{-}anti(Hep\text{-}Ag\text{-}platelet) \qquad (5)$$

where

Hep is defined as indicated above, and

Ag is pF4, one of its polymers, proteoglycan, a proteoglycan-pF4 complex or a mixture thereof.

To obtain the means A-H referred to above, blood platelets are cleaved orlyzed. Advantageously, the pF4, its polymers and proteoglycan-pF4 complexes are collected from lyzed blood platelets by binding to heparin-agarose gel and then elution of said gel, at a temperature of 15°–25° C., by means of an aqueous eluent having an ionic strength greater than or equal to 0.60 at a pH of 6.5–7.5.

According to the invention, the formation of the complex resulting from the reaction of said antigenic substance with said antibody material is detected by a method selected from the group consisting of the EIA, RIA, FIA and agglutination methods.

To develop reaction (1) or, in the specific case of the determination of heparin-induced thrombopenia, reactions (3)–(5), it is possible to carry out a so-called competitive EIA method or else a so-called sandwich EIA method according to a mechanism which comprises reacting said antigenic substance (1) with said antibody material (2) and then reacting the complex thus formed with a labeled anti(Ig) antibody, especially a labeled anti(IgA) antibody, a labeled anti(IgG) antibody or a labeled anti(IgM) antibody.

As an example of the determination of heparin-induced thrombopenia, the product of reactions (3)–(5), namely Ag-Hep-anti(Hep), Ag-Hep-anti(Hep-Ag) or Ag-Hep-anti-(Hep-Ag-platelet), will be reacted by the sandwich method with an antibody of the formula anti(Ig)-R*, where the labeling means R* comprises an enzyme detectable by an appropriate substrate; thus R* can be POD and the corresponding appropriate substrate can be OPD.

As an example of the determination of thrombopenia induced by heparin or one of the other inductor drugs, the antigenic substance $Ag_1$ according to the invention (advantageously bound to an appropriate support) will be reacted by the so-called competitive method with a mixture consisting of the anti(Y) antibody originating from the plasma to be studied, and an anti($Ag_1$)-R* antibody, where the labeling means R* comprises an enzyme detectable by an appropriate substrate, it being possible for R* to be POD and for the corresponding appropriate substrate to be OPD, as indicated above.

As a further example of the determination of thrombopenia induced by heparin or any other inductor drug, it will be possible to use an agglutination method in which the antigenic substance $Ag_1$, bound to an appropriate support (particles of latex, liposome, liposome fragment, bentonite, charcoal or colloidal gold or any other inert particles known in immuno-chemistry), is reacted with the patient's plasma containing the anti(Y) antibody. The agglutination can be measured by photometry or read off directly on a slide or in a tube.

As a variant, the resulting antigen/antibody complex, in which the antigen is bound to an appropriate support (preferably a wall), may be developed by reaction with a suitable labeled antibody (antibody labeled with an enzyme, a fluorogenic means, a radioisotope, a colored latex particle, colloidal gold, etc.).

From a practical point of view, when the variation in optical density is measured by means of a photometer, the dilution medium used to carry out reaction (1) and develop it is an aqueous medium whose optical density, for a normal plasma, is less than or equal to 0.2 and preferably less than or equal to 0.1. Such an initial optical density is preferably obtained with a plasma diluting medium which is a phosphate buffer containing goat's serum, the conditions used being a dilution of the normal subject's plasma and the pathological plasma to be studied of 1/50 to 1/100 (v/v) and a quantity of goat's serum of 5 to 10% by volume relative to said dilution medium. In other words, for a determination by a photometric method, the dilution medium used for the plasma to be studied will have an optical density which is less than or equal to 0.2 and preferably less than or equal to 0.1.

With the conventional dilution media, the optical density obtained for normal plasma under the same conditions is greater than or equal to 0.6, which does not enable the increase in the variation in optical density to be assessed correctly in the analysis relating to pathological plasmas.

The anti(Ig) and anti($Ag_1$) antibodies involved in carrying out the invention can be polyclonal or monoclonal antibodies. When monoclonal antibodies are used, it is possible (if desired, but this is not essentially necessary in practicing the present invention) to use their fragments F(ab) or F(ab')$_2$ in order to avoid any possible interaction with RF, since said RF is very sensitive towards the fragments Fc.

Finally, according to the invention, a kit is proposed for the determination of heparin-induced thrombopenia, which comprises at least one sample of said antigenic substance selected from the group consisting of monomeric pF4 having an average molecular weight of 8000 daltons, polymeric pF4, especially tetrameric pF4 having an average molecular weight of 32,000 daltons, proteoglycan having an average molecular weight of 56,000 daltons, and proteoglycan-pF4 complexes, especially the complex consisting of dimeric proteoglycan in which each proteoglycan group is bonded to 4 tetrameric pF4 groups, and having an average molecular weight of 368,000 daltons, or at least one sample of a complex of said antigenic substance with heparin, and, if appropriate, dilution media and other reagents.

Further advantages and characteristics of the invention will be understood more clearly from the description of the Examples which follow. These data as a whole do not in any way imply a limitation but are given by way of illustration.

EXAMPLE 1

Preparation of pF4

The starting material is a freezed platelet lyzate, which is washed and thawed three times in succession. The lyzate treated in this way is brought into contact with an aqueous solution containing ammonium sulfate (60% w/v); a precipitate is formed. The supernatant is collected and subjected to a dialysis operation. The dialyzate is deposited on a column of heparin-agarose gel and then eluted at RT by means of an aqueous eluent (salt gradient) whose ionic strength is greater than or equal to 0.60 at a pH of 6.5–7.5.

Elution with a salt gradient, with the aid of an automatic analyzer-separator, produces a chromatogram in the system OD at 280 nm eluted volume expressed in ml, in which the following are denoted:

the "dead" volume;

a first peak at 30 ml (injection of the salt gradient);

a first fraction of 60 to 90 ml relating to glycoproteins and traces of thrombospondin, with a maximum peak at 70 ml;

a second fraction of 90 to 132 ml relating mainly to thrombospondin, with a maximum peak at 100 ml (thrombospondin+glycoprotein) and a maximum peak at 112 ml (thrombospondin);

a third fraction of 132 to 180 ml relating mainly to βTG, with a maximum peak at 142 ml (glycoprotein) and a maximum peak at 170 ml (βTG); and a fourth fraction relating to pF4.

The fractions of peaks 70 (i.e. 70 ml), 100, 112, 142 and 170 and the pF4 fraction were tested with the supernatant before deposition and the dead volume after coating on to the walls or bottoms of microcells, against pathological plasmas from subjects suffering from well-characterized forms of thrombopenia induced by heparin, calcium heparinate or magnesium heparinate, and against plasmas from normal subjects, said plasmas being diluted to $\frac{1}{50}$–$\frac{1}{100}$ with a dilution medium (phosphate buffer to which 10% v/v of goat's serum has been added).

An immunoconjugate, namely an anti(Ig) antibody labeled with peroxidase [especially anti(IgA)-POD, anti(IgG)-POD and anti(IgM)-POD], was used to develop the reaction (sandwich EIA technique) and the coloration was then developed by means of the OPD/H$_2$O$_2$ couple.

The comparative reactivity of the normal plasmas and pathological plasmas demonstrated that the fraction containing pF4 was the most efficient at binding the anti(Y) autoantibody responsible for thrombopenia.

EXAMPLE 2

Determination of heparin-induced thrombopenia

The following protocol is recommended for the determination of thrombopenia induced by heparin and its metal salts.

A sandwich EIA technique is applied directly to plasma. The autoantibodies generated by Hep (here denoting heparin and/or its metal salts) and contained in the plasma are bound by the antigen, originating from platelets, in the presence of heparin (pF4-Hep) and developed by an anti(human Ig)-POD antibody [especially anti(IgA)-POD, anti(IgG)-POD or anti(IgM)-POD] and the coloration is then developed by means of the OPD/H$_2$O$_2$ couple.

Reagents

The assay kit comprises the following reagents:

precoated plate: a plate divisible into 6 ships of 16 cupulae each, coated with the pF4 antigen in the presence of Hep in a proportion of 2 to 8 µg/ml (preferably 5 µg/ml) of pF4 to 0.02 to 1 IU/ml (preferably 0.1 IU/ml) of Hep;

labeled anti(Ig): anti(human IgA, G or M) goat immunoglobulins coupled to peroxidase [namely anti(IgA)-POD, anti(IgG)-POD or anti(IgM)-POD];

dilution medium: a phosphate buffer containing 10% (v/v) of goat's serum;

wash solution: an aqueous solution containing the surfactant TWEEN® 20, concentrated 20-fold (to be diluted at the time of use);

OPD substrate: 5 to 10 tablets each containing 2 mg of OPD; and if appropriate, standardized reference samples for calibration, and a source of H$_2$O$_2$.

Operating principles

The plasmas to be tested, whether they be pathological or normal, are collected and treated as follows: removal of the plasma on 0.109M trisodium citrate, centrifugation for 10 minutes at 3000 rpm and recovery of the supernatant.

The sample of plasma to be tested must be diluted to $\frac{1}{50}$–$\frac{1}{100}$ with the dilution medium.

Procedure

1. Coating

The binding of the pF4-Hep antigenic substance is carried out in each cupula using 5 µg/ml of pF4 and 0.1 IU/ml of Hep.

2. Addition of the antibody

200 µl of the dilution medium containing the plasma to be tested (in which the autoantibody material responsible for Hep-induced thrombopenia is present) are added per cupula.

3. Incubation/washing

The reaction medium is incubated for 2 h at RT and then washed 3 times in succession with the wash solution, after the latter has been diluted.

4. Addition of the immunoconjugate

200 µl of immunoconjugate labeled with peroxidase are introduced into each cupula.

5. Incubation/washing

The resulting reaction medium is incubated for 2 h at RT and then washed 3 times in succession with the diluted wash solution.

6. Staining

200 μl of the OPD/H$_2$O$_2$ couple are added per cupula, the reaction medium is incubated for 3 minutes at RT, the reaction is stopped by the addition of 50 μl of 3M H$_2$SO$_4$ per cupula and the OD value is read off at 492 nm.

EXAMPLE 3

Correlation

Clinical trials were carried out in parallel in accordance with the protocol of Example 2 by comparison with the prior art involving the agglutination of blood platelets with heparin. To this end, the plasma from each hospitalized patient assumed to be suffering from heparin-induced thrombopenia was separated into two batches, one for each technique. The results obtained are collated in Table I below.

These results demonstrate that (i) when the platelet aggregation test with heparin is doubtful, the determination according to the invention makes it possible to remove the doubt: thrombopenia for patients n° 4 and 15, absence of thrombopenia for patients n° 2 and 25;

(ii) the determination according to the invention makes it possible to mitigate the diagnostic errors of the aggregation test for patients n° 14 and 16 (who manifestly did not have heparin-induced thrombopenia) and patients n° 17 and 22 (who manifestly were suffering from heparin-induced thrombopenia); and (iii) there is a good correlation in the results obtained for the remainder of the patients.

These clinical trials demonstrate the advantage of the determination of thrombopenia according to the invention, as far as rapidity and reliability are concerned, compared with the platelet aggregation technique of the prior art.

EXAMPLE 4

Other clinical trials

A second series of clinical trials was carried out in accordance with the protocol of Example 2 on a batch of plasma from patients suffering from heparin-induced thrombopenia, by comparison with a batch of plasma from normal subjects. In this second series of trials, the plasmas from 21 thrombopenic patients and 32 normal subjects were used, the antigenic substance being a pF4-heparin complex prepared in the following proportions: 5 μg/ml of pF4 and 0.1 IU/ml of calcium heparinate.

The results show the advantage of adding 10% v/v of goat's serum to the dilution medium in order to have an OD which is always less than 0.1 for the normal plasmas. If the OD of the normal plasmas diluted to 1/50 or to 1/100 is greater than 0.3 or even 0.6, it becomes difficult to assess the OD of the thrombopenic plasmas with a photometer.

TABLE I

| Patient | Determination according to the invention | | Aggregation test with heparin |
|---|---|---|---|
| | (a) | (b) | (c) |
| 1 | 0.65 | 0.45 | A |
| 2 | 0.20 | 0.10 | B |
| 3 | 0.11 | 0.09 | C |
| 4 | 0.24 | 0.15 | B |
| 5 | 0.81 | 0.52 | A |
| 6 | 0.59 | 0.34 | A |
| 7 | 0.88 | 0.60 | A |

TABLE I-continued

| Patient | Determination according to the invention | | Aggregation test with heparin |
|---|---|---|---|
| | (a) | (b) | (c) |
| 8 | 0.60 | 0.39 | A |
| 9 | 0.73 | 0.74 | A |
| 10 | 1.58 | 0.93 | A |
| 11 | 1.65 | 1.12 | A |
| 12 | 1.17 | 1.03 | A |
| 13 | 0.79 | 0.60 | A |
| 14 | 0.17 | 0.10 | A |
| 15 | 0.70 | 0.32 | B |
| 16 | 0.20 | 0.13 | A (d) |
| 17 | 0.67 | 0.44 | C |
| 18 | 0.80 | 0.53 | A |
| 19 | 0.57 | 0.46 | A |
| 20 | 0.15 | 0.10 | C |
| 21 | 0.72 | 0.38 | A |
| 22 | 0.62 | 0.42 | C |
| 23 | 0.51 | 0.31 | A |
| 24 | 1.64 | 1.30 | A |
| 25 | 0.13 | 0.10 | B |
| Control (e) | 0.12 (0.06–0.21) | 0.08 (0.04–0.13) | — |

Notes
(a) with plasma diluted to 1/50;
(b) with plasma diluted to 1/100;
(c) with the following notation: A positive result; B doubtful result; C negative result;
(d) result evaluated incorrectly as positive (error due to the patient being pregnant);
(e) carried out on plasma from a normal subject: mean value and range.

What is claimed is:

1. A method of diagnosing heparin-induced thrombocytopenia induced by a heparin drug, Hep, selected from the group consisting of heparin, metal heparinates, heparinoids, and heparin fragments, wherein the heparin fragments have an average molecular weight of less than 6,000 daltons, said method comprising:

taking a sample suspected of containing heparin-induced anti(Ag-Hep) antibodies from a patient, wherein Hep is the heparin drug defined above, Ag is an antigenic substance that forms an Ag-Hep complex with Hep, and Ag represents an antigenic substance selected from the group consisting of
(a) platelet factor 4 (pF4),
(b) fractions containing pF4,
(c) recombinant pF4,
(d) synthetic peptides corresponding to the carboxy-terminal amino acids 1–13 or 13–24 of pF4,
(e) proteoglycan,
(f) proteoglycan-pF4 complexes, and
(g) mixtures thereof;

admixing with the sample an Ag-Hep complex as defined above;

and detecting a reaction between the anti(Ag-Hep) antibodies in the sample and the Ag-Hep complex which indicates heparin-induced thrombocytopenia.

2. A method according to claim 1, wherein the antigenic substance is (d) synthetic peptides which correspond to the carboxy-terminal amino acids 1–13 or 13–24 of pF4.

3. A method according to claim 1, wherein the antigenic substance is (a) pF4.

4. A method according to claim 1, wherein the antigenic substance is (f) proteoglycan-pF4 complexes wherein said complexes consist of dimeric proteoglycan in which each proteoglycan group is bonded to 4 tetrameric pF4 groups and the proteoglycan-pF4 complexes have an average molecular weight of 368,000 daltons.

5. A method according to claim 1, wherein the detection step is performed by further reacting a labeled anti(Ig) antibody with the reaction complex formed between the anti(Ag-Hep) antibodies in the sample and the Ag-Hep complex.

6. A method according to claim 5, wherein the labeled anti(Ig) antibody is selected from the group consisting of anti(IgA), anti(IgG), and anti(IgM) antibodies labeled with peroxidase.

7. A method according to claim 1, further comprising diluting the sample with a medium such that the diluted sample has an optical density less than or equal to 0.2 at a concentration of 1/50–1/100 (v/v) in said medium before admixing with the Ag-Hep complex and detecting the reaction complex photometrically.

8. A method according to claim 7, wherein the optical density is less than or equal to 0.1.

9. A method according to claim 7, wherein the diluting medium is a phosphate buffer containing goat's serum.

10. A method of diagnosing heparin-induced thrombocytopenia induced by a heparin drug, Hep, selected from the group consisting of heparin, metal heparinates, heparinoids, and heparin fragments, wherein the heparin fragments have an average molecular weight of less than 6,000 daltons, said method comprising:

taking a sample suspected of containing heparin-induced anti(Ag-Hep) antibodies from a patient, wherein Hep is the heparin drug defined above, Ag is an antigenic substance that forms an Ag-Hep complex with Hep, and Ag represents an antigenic substance selected from the group consisting of
(i) platelet factor 4 (pF4),
(ii) low affinity pF4 and $\beta$-thromboglobulin,
(iii) peptidic fractions comprising the carboxy-terminal peptides 1–13 or 13–24 of pF4,
(iv) proteoglycan,
(v) proteoglycan-pF4 complexes, and
(vi) mixtures thereof;

admixing with the sample an Ag-Hep complex as defined above;

and detecting a reaction between the anti(Ag-Hep) antibodies in the sample and the Ag-Hep complex which indicates heparin-induced thrombocytopenia.

11. A method according to claim 10, wherein the antigenic substance (v) proteoglycan-pF4 complexes which consist of dimeric proteoglycan in which each proteoglycan group is bonded to 4 tetrameric pF4 groups and the proteoglycan-pF4 complexes have an average molecular weight of 368,000 daltons.

* * * * *